(12) United States Patent
Vogeser (10) Patent No.: US 8,337,704 B2
(45) Date of Patent: *Dec. 25, 2012

(54) MANIPULATION OF MAGNETIC MICROPARTICLES IN A HIGH PRESSURE LIQUID SYSTEM AND EXTRACTION PROCESS

(75) Inventor: Michael Vogeser, Munich (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 433 days.

This patent is subject to a terminal disclaimer.

(21) Appl. No.: 12/328,228

(22) Filed: Dec. 4, 2008

(65) Prior Publication Data

US 2010/0291712 A1 Nov. 18, 2010

(30) Foreign Application Priority Data

Dec. 7, 2007 (EP) ..................................... 07023765

(51) Int. Cl.
*B03C 1/02* (2006.01)
*G01N 1/34* (2006.01)
*G01N 21/00* (2006.01)

(52) U.S. Cl. ..... 210/695; 210/635; 210/806; 210/198.2; 210/257.1; 210/259; 210/295; 422/68.1; 422/70; 422/82.05; 422/82.08; 422/527; 436/526

(58) Field of Classification Search .................. 436/526; 422/68.1, 70, 82.05, 82.08, 527; 210/635, 210/695, 806, 198.2, 257.1, 259, 295

See application file for complete search history.

(56) References Cited

U.S. PATENT DOCUMENTS 7,033,473 B2 * 4/2006 Gascoyne et al. ............ 204/547
2002/0036141 A1 3/2002 Gascoyne et al.
(Continued)

FOREIGN PATENT DOCUMENTS

EP 2068143 A1 6/2009
WO 2007009519 A1 1/2007

OTHER PUBLICATIONS

Franzreb, M. et al., "Protein purification using magnetic adsorbent particles," Appl Microbiol Biotechnol 70 (2006) 505-516.

(Continued)

*Primary Examiner* — David A Reifsnyder
(74) *Attorney, Agent, or Firm* — Roche Diagnostics Operations, Inc.

(57) ABSTRACT

The invention concerns a device and a method for the manipulation of a liquid sample material in which magnetic microparticles are suspended whereby the microparticles have a functionalized surface and an analyte is bound to the surface. The sample material is introduced into a device with a liquid system through an injection device (50) and in a first mobile phase the sample material is carried to an extractor (90). In a first section (97a) of the extractor (90) the microparticles are immobilized by means of a magnetic field of a controllable device (96) and separated from the remaining sample material. By switching over of a switching unit (110) a second mobile phase (75) is carried to the extractor (90) and the second mobile phase (75) detaches the adsorbed analyte from the surface of the microparticles. In a second section (97b) of the extractor (90) the microparticles are immobilized and the second mobile phase (75) with the dissolved analyte(s) can be analyzed by way of chromatographic separation (130) and subsequent detection (140).

13 Claims, 9 Drawing Sheets

U.S. PATENT DOCUMENTS

2003/0168392 A1     9/2003    Masuda et al.
2010/0326909 A1*   12/2010   Vogeser ........................ 210/222

OTHER PUBLICATIONS

Hubbuch, J. et al., "High-Gradient Magnetic Affinity Separation of Trypsin from Porcine Pancreatin," Biotechnology and Bioengineering 79:3 (Aug. 5, 2002) 301-313.

Vogeser, M. et al., "Determination of Itrconazole and Hydroxyitraconazole in Plasma by Use of Liquid Chromatography-Tandem Mass Spectrometry with On-line Solid Extraction," Clin Chem Lab Med 41:7 (2003) 915-920.

EPO Search Report dated Feb. 10, 2011 for EP Application No. 08 02 1245.

* cited by examiner

MANIPULATION OF MAGNETIC MICROPARTICLES IN A HIGH PRESSURE LIQUID SYSTEM AND EXTRACTION PROCESS

RELATED APPLICATIONS

This application claims priority to European application EP 07023765.6 filed Dec. 7, 2007.

FIELD OF THE INVENTION

The present invention concerns the automation of extraction processes by means of magnetic microparticles with a functionalized surface. Particularly, the invention concerns a device and a method for the manipulation of a liquid sample material in which magnetic microparticles are suspended whereby the microparticles have a functionalized surface and an analyte is bound to the surface. The sample material is introduced into a device with a liquid system through an injection device (50) and in a first mobile phase the sample material is carried to an extractor (90). In a first section (97a) of the extractor (90) the microparticles are immobilized by means of a magnetic field of a controllable device (96) and separated from the remaining sample material. By switching over of a switching unit (110) a second mobile phase (75) is carried to the extractor (90) and the second mobile phase (75) detaches the adsorbed analyte from the surface of the microparticles. In a second section (97b) of the extractor (90) the microparticles are immobilized and the second mobile phase (75) with the dissolved analyte(s) can be analyzed by way of chromatographic separation (130) and subsequent detection (140).

BACKGROUND

U.S. 2003/0168392 A1 discloses a multi-dimensional liquid chromatograph separation system. The analytes are separated on a first analysis system consisting of a first column and a first mobile phase, and are trapped on trapping columns. The trapped analytes are subsequently loaded onto the second analysis system consisting of a second column and a second mobile phase. The document discloses the trapping and loading mechanism consisting of a combination of switching valves necessary to produce the serial separations.

An overview on the purification of proteins using magnetic adsorbent particles is given by Franzreb M., et al. Appl. Microbiol. Biotechnol. 70 (2006) 505-516. Particularly, Hubbuch, J. J., et al. Biotechnol Bioeng 79 (2002) 301-313 describe a high-gradient magnetic separation system comprising a filter chamber filled with woven wire mesh of steel, whereby the filter chamber is positioned between the plane pole shoes of an electromagnet which can be switched on or off. The filter chamber comprises two openings at opposite ends, at the top and the bottom of the chamber. The two openings of the filter chamber are fluidically connected and a pump is integrated in the fluidic connection. Thereby a loop is formed such that a liquid phase can be cycled within the loop. Between the pump and the bottom opening of the chamber the authors disclose a three way valve, suitable for fluidically connecting the filter chamber with a batch reactor and a first buffer reservoir. Between the pump and the top opening of the filter chamber a four way valve is disclosed, the valve being suitable for making a fluidic connection with a second or a third buffer reservoir, or a fraction collector. The authors further disclose the use of such a fluidic system for purifying trypsin from crude pancreatin. To this end, magnetic particles functionalized with benzamidine are incubated in the batch reactor with a suspension of crude pancreatin, whereby trypsin is adsorbed to the particles. The suspension with the magnetic particles is fed into the loop together with binding buffer. The suspension is circulated in the loop and passed through the filter chamber several times with the electromagnet being switched on, whereby the magnetic particles are immobilized in the filter chamber. Subsequently, the liquid phase is exchanged by a washing buffer, the immobilized magnetic particles are released by switching the magnet off, and circulated in the loop with the washing buffer. During the washing step trypsin remains adsorbed to the magnetic particles. After a further immobilization step, the washing buffer is substituted with an elution buffer and elution is performed by again releasing the magnetic particles and circulating buffer and particles in the loop. The last step is the recovery of the elution buffer with trypsin from the system while the magnetic particles are retained in the filter chamber.

WO 2007/009519 discloses a system in which the separation chamber comprises, between two frits, a fluidic-bed of functionalized magnetic particles. A magnetic field can be applied and as a result the magnetic particles are immobilized at the walls of the separation chamber. A liquid phase containing an analyte is circulated through the separation chamber. Washing and elution steps can be performed.

For the majority of in-vitro diagnostic analyses it is necessary to extract one or more target analytes from complex sample materials (serum, plasma, whole blood, urine etc.). In this connection the respective target analytes are concentrated by different processes whereas components of the sample matrix which would hinder the subsequent analysis (e.g. proteins, peptides, salts) are depleted. The following extraction methods have been previously used to concentrate target analytes: protein precipitation with organic solvents or acids; liquid-liquid extraction (solvent extraction) with an evaporation step; solid phase extraction on cartridges which contain particles with defined surface structures (especially hydrocarbon-functionalized silica particles; solid phase extraction, SPE).

Extraction methods known from the prior art require a large amount of manual work. Methods for automating such extraction processes have up to now been technically very elaborate and have numerous disadvantages. They require, on the one hand, very demanding mechanical constructions e.g. pipetting systems and/or vacuum systems. On the other hand, the known methods require a large amount of solid and liquid consumables e.g. extraction cartridges, extraction plates, solvents. Furthermore, they require a long processing period and are characterized by a low sample throughput and limited series lengths.

An important aim of the work towards the present invention was to develop an extraction system which, in combination with a separation and analytical system, forms a substantially closed system. The liquid system according to the invention which is preferably a high pressure liquid system overcomes the limitations of current automated extraction processes.

SUMMARY OF THE INVENTION

A general aspect of the invention is a device for the separation of magnetic or paramagnetic microparticles and the elution of an analyte adsorbed on said particles, the device being a liquid system (LS) comprising means for making fluidic connections (30), a first and a second inlet (10, 20), a rotary valve switching unit suitable for producing two different fluid connecting states (110), and an extractor (90) with an entry port (91) and an exit port (92), and with a controllable device (96) which can be used to temporarily apply a local magnetic field, characterized in that the extractor comprises a fluid connecting line (95) between the entry port (91) and the exit port (92), and the controllable device (96) is capable of temporarily applying a local magnetic field to two or more consecutive sections (97) of the line (95).

A further aspect of the invention is a device with a liquid system (LS) comprising means for making fluidic connections (30), a first and a second inlet (10, 20), at least one pressure-generating means (40), an injection device (50), two storage containers (60, 70) for a first and a second mobile phase (65, 75) in a liquid state of aggregation, a collecting vessel (80), an extractor (90), an outlet (100) and a means suitable for producing two different fluid connecting states (switching unit (110), characterized in that the first inlet (10) is designed such that the first mobile phase (65) can be fed under pressure from the first storage container (60) to the LS via a fluidic connection; the first inlet (10) is additionally fluidically connected to an injection device (50), the injection device being designed such that it allows a mixture (120) of liquid sample material (121) and microparticles suspended therein (122) to be introduced into the first mobile phase that was introduced through the inlet; the second inlet (20) is designed such that the second mobile phase (75) can be fed under pressure from the second storage container (70) to the LS via a fluidic connection; the first inlet (10) is connected to a first entry port (E1) of the switching unit (110) and the second inlet (20) is fluidically connected to a second entry port (E2) of the switching unit; the extractor (90) has one entry port (91) and one exit port (92) where the entry port (91) of the extractor is fluidically connected to a first exit port (A1) of the switching unit and the exit port (92) of the extractor is fluidically connected to a third entry port (E3) of the switching unit; the extractor additionally comprises a fluid connecting line (95) between the entry port (91) and the exit port (92), also a controllable device (96) which can be used to temporarily apply a local magnetic field to two or more consecutive sections (97a, 97b) of this line; the second exit port (A2) of the switching unit (110) is the outlet (100) or is fluidically connected to the outlet (100); the third exit port (A3) of the switching unit (110) is fluidically connected to the collecting vessel (80); and the switching unit (110) is suitable in a first connecting state (I) for fluidically connecting E1 and A1, E2 and A2 as well as E3 and A3 and in the second connecting state (II) it is suitable for fluidically connecting E2 and A1, E3 and A2 as well as E1 and A3.

Yet, a further aspect of the invention is the use of the device according to the invention for the manipulation of magnetic microparticles and two different mobile phases in a liquid state of aggregation.

Yet, a further aspect of the invention is a method for obtaining a purified analyte from a complex liquid sample material containing the said analyte comprising the steps (a) contacting the liquid sample material (121) containing the analyte with microparticles (122) made of a magnetic or paramagnetic material with a functionalized surface (123) whereby the analyte adsorbs to the surface; followed by (b) introducing the sample material with the microparticles into a device according to the invention using the injection device (50); followed by (c) pumping a first mobile phase (65) from a first storage vessel (60) into the first inlet (10) of the device where the switching unit (110) of the device makes the connecting state (I) and in the extractor (90) a magnetic field is applied to a first section (97a) of the line (95) located therein which is suitable for immobilizing the magnetic or paramagnetic microparticles (122) contained in the mobile phase entering through the line (95) on the nearest inner wall (93) of the line (95) facing the magnetic field in the first section (97a); followed by (d) immobilizing the microparticles (122) in the extractor (90) in the first section (97a) of the inner wall (93) of the line (95); followed by (e) separating the microparticles (122) from the remaining sample material by further pumping the first mobile phase (65) from the first storage vessel (60) into the first inlet (10) whereby the immobilized microparticles are washed and the remaining sample material is fed into the collecting container (80); followed by (f) switching over the switching unit (110) into the connecting state (II) and pumping a second mobile phase (75) from the second storage vessel (70) into the second inlet (20) of the device where the second mobile phase (75) is suitable for detaching the adsorbed analyte from the surface of the microparticles (122); followed by (g) eluting the analyte by contacting the microparticles (122) with the second mobile phase (75) and at the same time weakening or removing the magnetic field from the first section (97a) of the line (95) in the extractor (90) and moving the microparticles (122) in the line (95) towards a second section (97b) of the line (95) by the movement of the mobile phase (75); (h) applying a magnetic field to the second section (97b) of the line (95) where the magnetic field is suitable for immobilizing magnetic or paramagnetic microparticles (122) contained in the mobile phase entering through the line (95) on the nearest inner wall (93) of the line (95) facing the magnetic field in the second section (97b); followed by (i) immobilizing the microparticles (122) on the inner wall (93) in the second section (97b) of the line; followed by (k) moving the second mobile phase containing the eluted analyte to the outlet (100) of the device by further pumping the second mobile phase (75) from the second storage vessel (70) into the second entry port (20) by means of which the analyte is obtained in a purified form at the outlet (100).

Yet, a further aspect of the invention is a method for detecting an analyte in a complex liquid sample material containing the said analyte comprising the steps (a) providing a device which is characterized in that the outlet (100) of the HLS is fluidically connected to a separation unit (130) and the separation unit is fluidically connected to a detector (140), and the exit port (145) of the detector is fluidically connected to the collecting vessel (80). (b) Preparing the purified analyte from the sample material using a device according to the invention wherein the analyte is obtained in a purified form at the outlet (100) of the device and the switching unit (110) makes the connecting state (II); (c) moving the second mobile phase containing (i) the analyte and (ii) optionally further substances eluted together with the analyte through the separation unit (130) and into the detector (140) where the movement is driven by pumping the second mobile phase (75) from the second storage vessel (70) into the second entry port (20); (d) detecting the analyte by the detector (140).

BRIEF DESCRIPTION OF THE FIGURES

FIG. 3: Enlarged section from FIG. 1 and FIG. 2 which shows the two connecting states that can be made by the switching unit (110). In state (I) A1 and E1, A2 and E2 as well as A3 and E3 are simultaneously fluidically connected; in state (II) A3 and E1, A1 and E2 as well as A2 and E3 are simultaneously fluidically connected. B—Particularly preferred form of the extractor (90) in which the line (95) between the entry port (91) and exit port (92) of the extractor (90) has a helical configuration with two or more windings (99a, 99b) where one or more sections (97e) of the windings and the respective sections (97a, 97b) of the line leading to the entry port (91) and exit port (92) are arranged side by side.

FIG. 5: Schematic representation of the action of the extractor (90). A—A magnetic field mediated by the device (96) (symbolized by the horizontal texture of (96)) is applied to the area (97a) and immobilizes the extraction particles with the adsorbed substances to the side of the inner wall (93) of the line (95) facing the magnetic field. At the same time the first mobile phase (65) together with the remaining sample material is moved towards the outlet of the extractor and the collecting vessel (80). During this operating step the extraction particles are separated from the remaining sample material. Since in this process additional first mobile phase is continuously pumped into the LS, the particles are finally completely surrounded by the first mobile phase. B—Subsequently the extraction particles with the adsorbed analyte are brought into contact with the second mobile phase and the magnetic field is switched off (or sufficiently reduced) so that the extraction particles are again mobilized by the flow of the second mobile phase in the line (95) and reach the loop (99). This area is shown in which the adsorbed substances (124, 125) are in the process of being detached from the extraction particles (122). This process takes place continuously while the extraction particles pass through the loop (99); C—Subsequently the extraction particles are transported by the flow of the second mobile phase (75) through the line (95) to the area (97b) where they are again immobilized by a magnetic field (generated using (96)). The substances detached from the extraction particles including the analyte are now present in a purified form in the second mobile phase. They are subsequently again transported in the direction of flow in order to for example pass through an analytical separation device and a detector.

FIG. 7: A possible and preferred embodiment of the extractor comprises an electromagnet with a toroidal core transformer (98). The electromagnet can for example be actuated by a control device where the control device preferably also sets the switching states of the switching unit (110). The loop of the line of the extractor is configured in the form of a first and second winding (99a, 99b). Further windings can be added to increase the holding time of the extraction particles in the loop. The line that is actually used in this extractor consists of a HPLC tube made of polyphenyl sulfone (PPSU). The entry port (91) and exit port (92) of the extractor are provided with couplings. In the example shown there are three areas in which the extraction particles can be immobilized by applying a magnetic field, 97a, 97b and 97c.

DETAILED DESCRIPTION OF THE INVENTION

The invention provides a liquid system which can be used to manipulate magnetic or paramagnetic microparticles and two different mobile phases, preferably liquid phases. As an example the present invention is illustrated on the basis of the use of corresponding microparticles with a hydrocarbon-functionalized surface. Such microparticles have previously not been used for quantitative analyses in clinical chemistry. However, they have considerable advantages when preparing clinical sample material. These advantages are particularly manifest when the aim is to detect analytes having a low molecular weight, typically between 50 and 1000 Daltons. A person skilled in the art can profit from using such particles especially in a quantitative chromatographic analysis.

In a simple form of sample preparation, magnetic or paramagnetic microparticles (extraction particles) with hydrocarbon-functionalized surfaces are brought into contact with liquid sample material for example whole blood, serum, plasma or haemolysed blood in a reaction vessel. Subsequently the analyte is adsorbed from the liquid phase onto the functionalized surface of the particles. After a certain holding time the solid and liquid phases are separated from one another. This can preferably take place by removing the liquid phase from the vessel while the particles are retained in the vessel by a magnetic field. For example a permanent magnet can be moved from outside to the wall of the vessel such that the magnetic particles are immobilized at this site on the vessel inner wall. The particles can be subsequently washed.

For this purpose the magnet can for example be removed and after that the particles are resuspended in a washing buffer. After a renewed immobilization of the particles and removal of the washing buffer, the analyte is eluted from the surface of the particles by contacting the microparticles with a solvent suitable for the desorption of the analyte. After separating the solid and liquid phases, the analyte can be detected from the solvent using chromatographic methods.

The direct automation of the manual operating steps as described above does not yet eliminate the disadvantages of the prior art in a satisfactory manner. In contrast, the present invention describes a method for automating the extraction in a liquid system, preferably a high pressure liquid system, which surprisingly has many advantages. In particular the device according to the invention requires a minimum of moving parts and thus makes the use of complicated pipetting units that can be moved in three dimensions or complicated vacuum system superfluous.

A particularly preferred embodiment of the present invention is a substantially closed high pressure liquid system and the use of the same to manipulate magnetic or paramagnetic microparticles suspended in a liquid sample material and two different mobile phases. A substantially closed system in the sense of the present invention is a high pressure liquid system in which there is no operationally open connection between the space filled by the mobile phase and the environment. The high pressure liquid system according to the invention is a substantially closed system because it has an injection device which allows a mixture of liquid sample material and extraction particles to be introduced in a controlled manner into the liquid system.

According to the invention two different mobile phases are used. The first mobile phase is selected such that it can be used to separate extraction particles and the remaining sample material. In this connection "remaining sample material" means the material from the liquid sample from which at least portions of the analyte contained therein have been extracted by adsorption to the extraction particles. The second mobile phase is used to detach the analyte from the extraction particles. In this connection it is preferred that the first and second mobile phase have a liquid state of aggregation or are each in a liquid state of aggregation in the high pressure liquid system according to the invention. This also implies the use of mobile phases which are volatile at room temperature and normal ambient pressure.

When the high pressure liquid system according to the invention is used, the material that is introduced remains within the system from the time at which the mixture of extraction particles and sample material is injected until the chromatographic analysis of the analyte.

The described process allows magnetic or paramagnetic microparticles which are used for extraction for analytical purposes to be simply manipulated preferably in the high pressure liquid system according to the invention. An automated operation of the device according to the invention is readily possible. The principle of manipulating the microparticles allows analytical extraction systems to be constructed in which a minimum of moved components have to be used. In particular complicated x-y-z pipetting units or vacuum systems are no longer necessary in contrast to the previously common automated extraction systems. Moreover, the system according to the invention can be extremely compactly configured and the requirement for solid or liquid consumables is minimized. Furthermore, the closed system design allows the use of liquid phases with a relatively high vapour pressure which would lead to problems in open systems such as automated pipettors for example due to the build up of pressure by evaporation of the liquid phase in the pipetting chamber. Compared to previous systems, the system according to the invention also enables very short cycle times and thus a high sample throughput.

Figure 2:
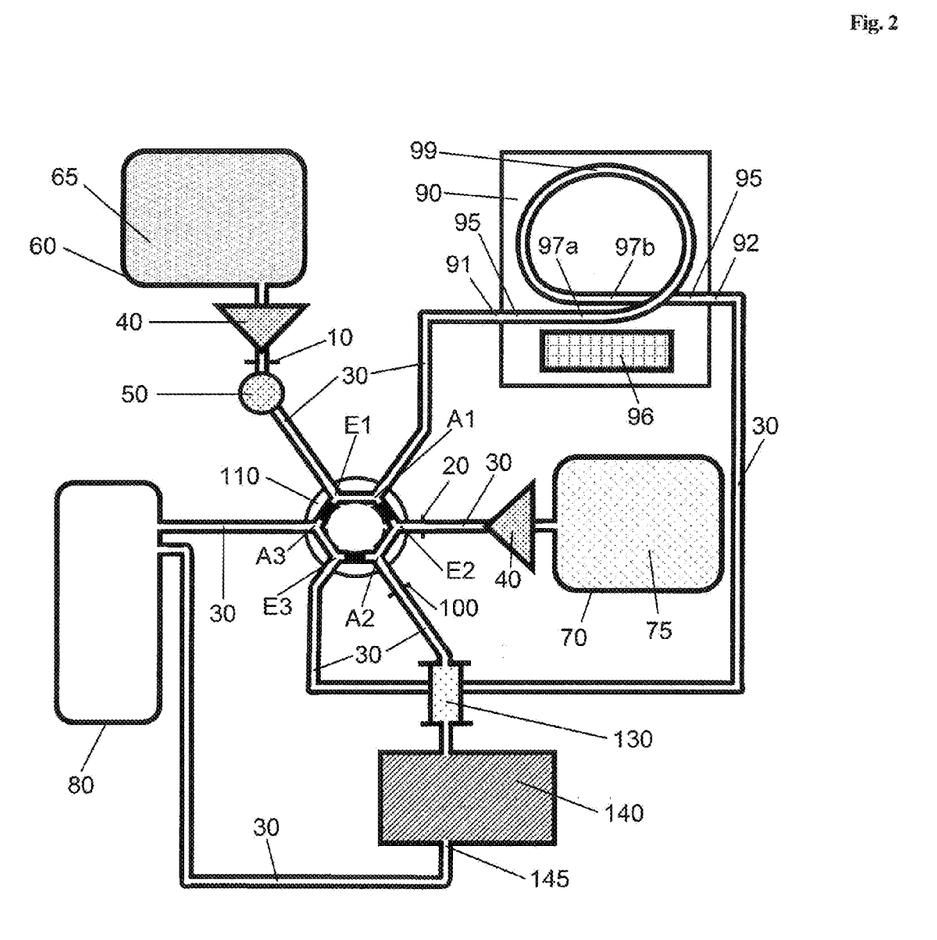
FIG. 2: referred high pressure LS (HLS) in which the HLS is a substantially closed system and the outlet (100) is fluidically connected to a separator unit (130) and the separating unit is fluidically connected to a detector (140) and the exit port (145) of the detector is fluidically connected to the collecting vessel (80). With regard to the extractor reference is made to the description of FIG. 1.
Figure 3A:
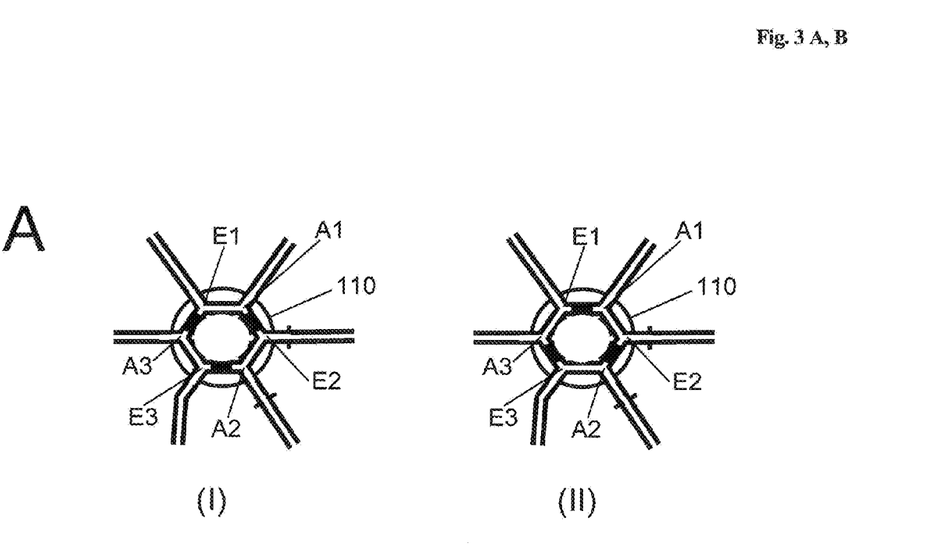
Figure 3B:
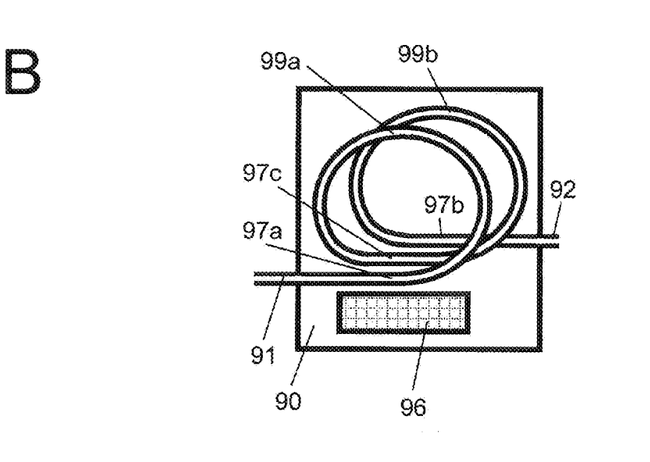
Figure 4:
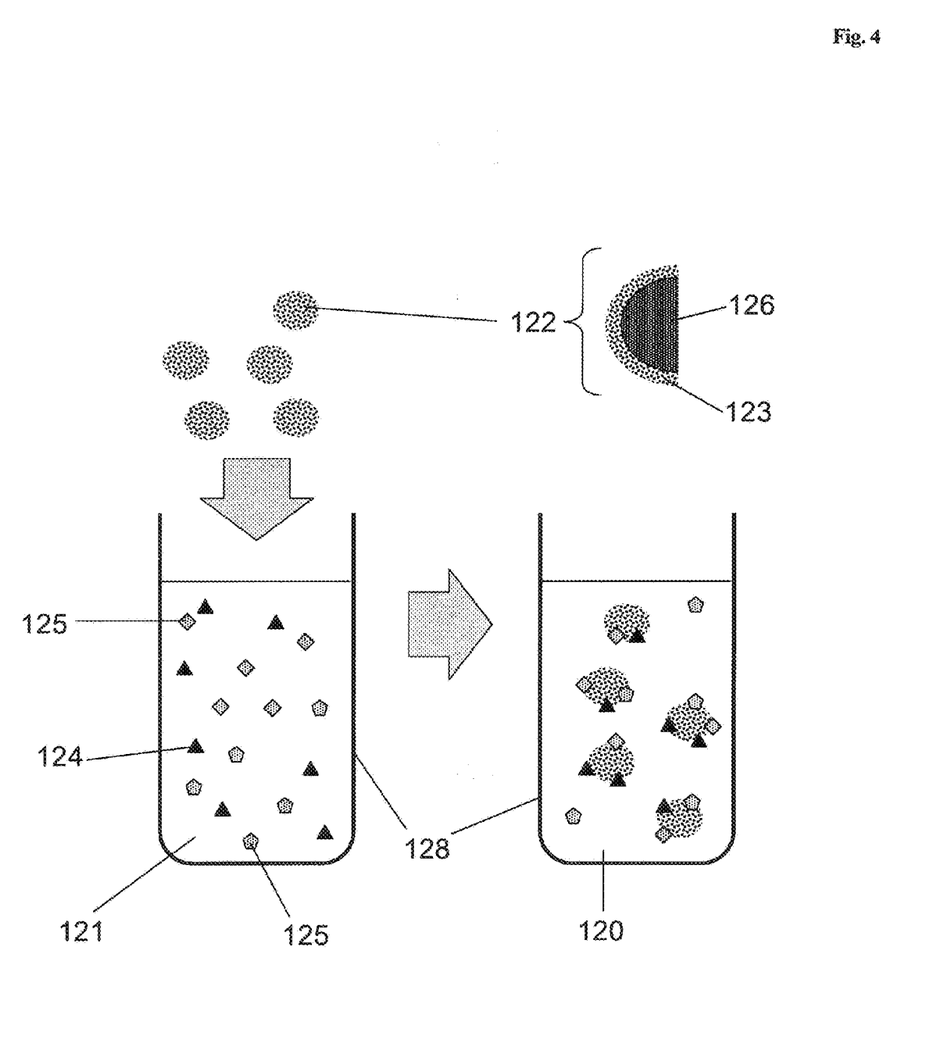
FIG. 4: Schematic representation of the extraction particles (122) and their use for the adsorption of the analyte (124) and optionally further substances (125) contained in the liquid sample material (121) which can adsorb to the surface (123) of the extraction particles. For this purpose the surface (123) of the extraction particles is functionalized e.g. in a particularly preferred embodiment it is coated at least partially with a hydrophobic layer. The core of the extraction particles contains a magnetic or paramagnetic material. The mixture (120) of sample material (121) and extraction particles (122) with adsorbed analyte (124) is introduced into the device according to the invention using the injection device (50) see FIG. 1 and FIG. 2.
Figure 5A:
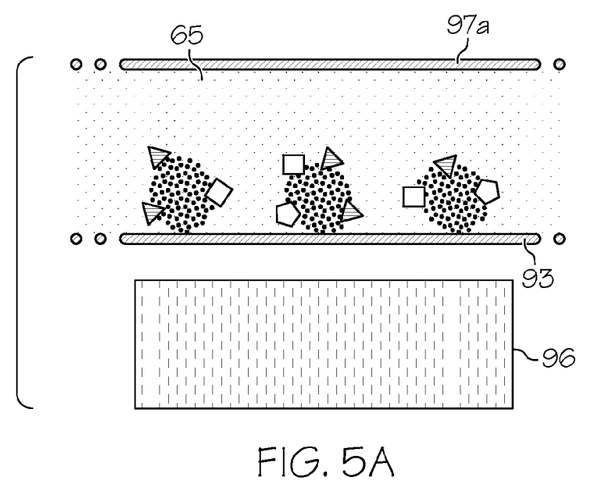
Figure 5B:
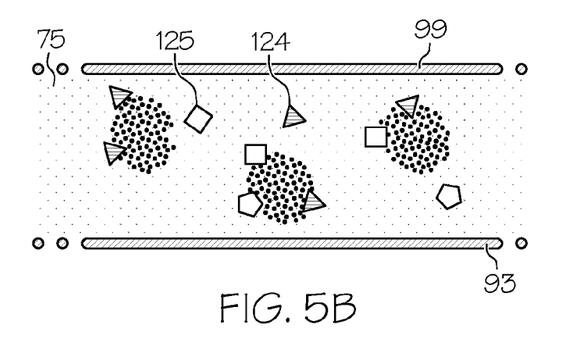
Figure 5C:
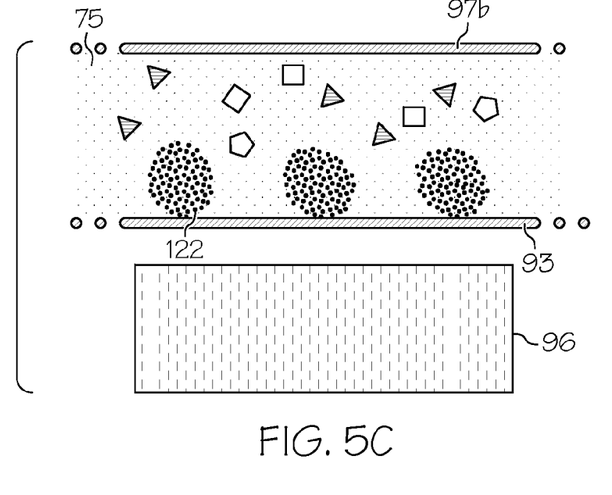
Figure 6A:
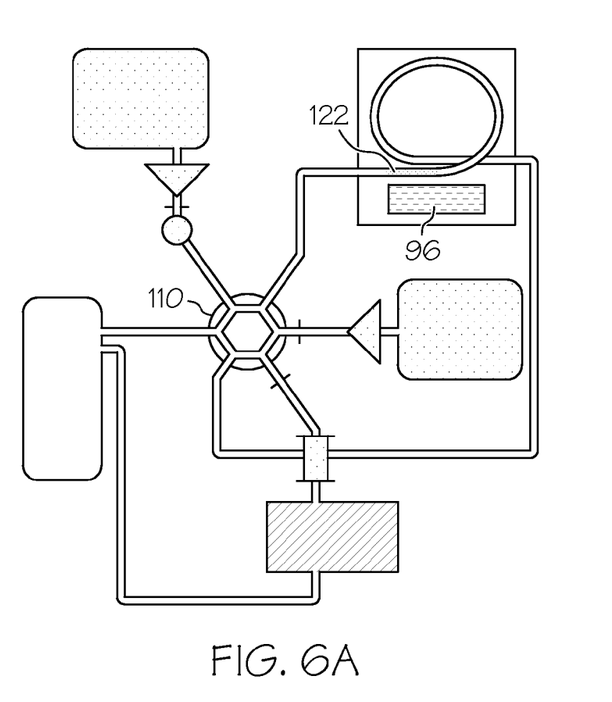
FIG. 6: Schematic representation of the process of sample purification by means of the device according to the invention shown in FIG. 2. The elements of the device that are shown correspond exactly to the elements shown in FIGS. 1, 2 and 3 and described in relation thereto. The steps shown in A-D are described in example 1.
Figure 6B:
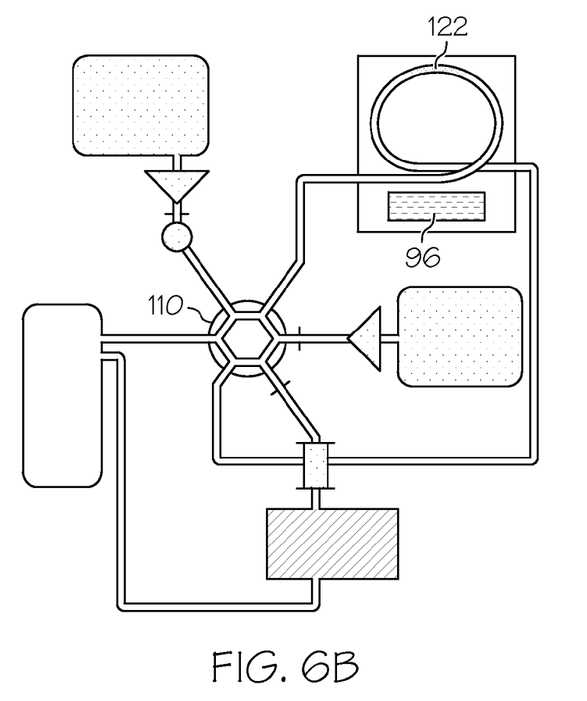
Figure 6C:
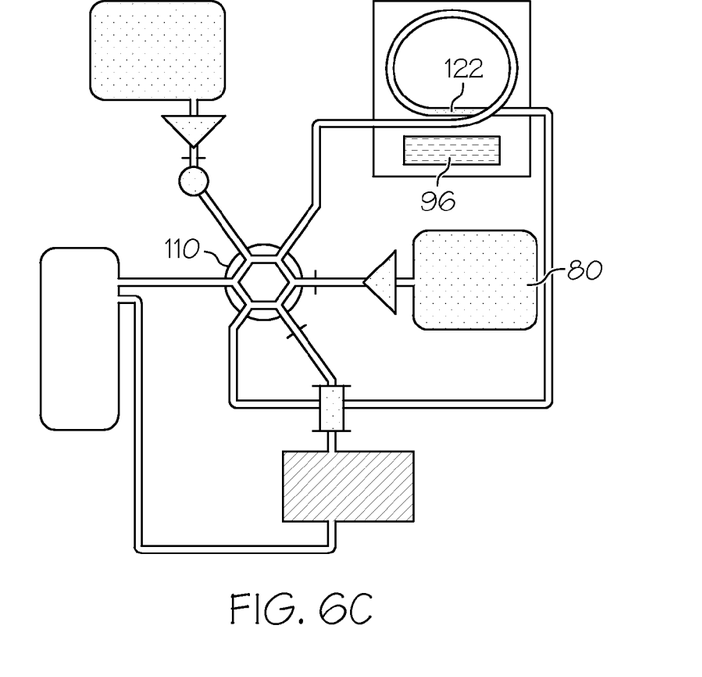
Figure 6D:
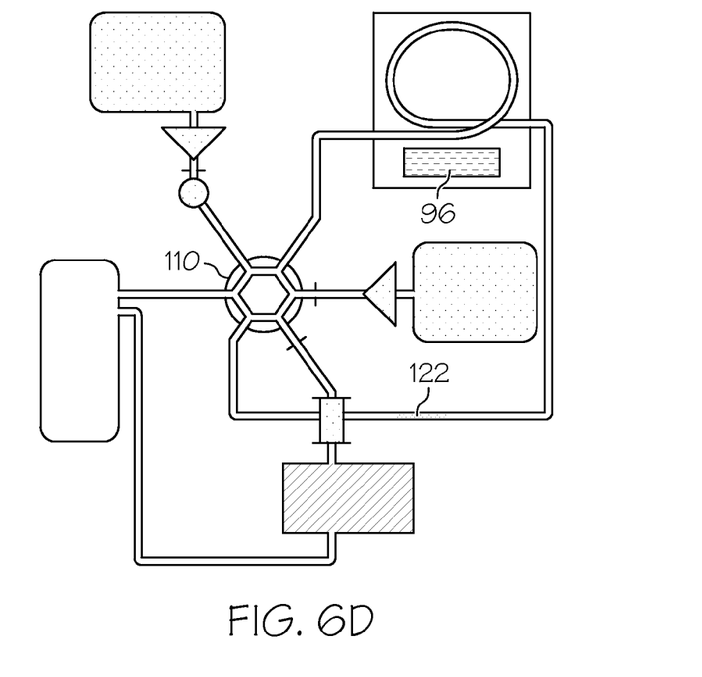
Figure 7:
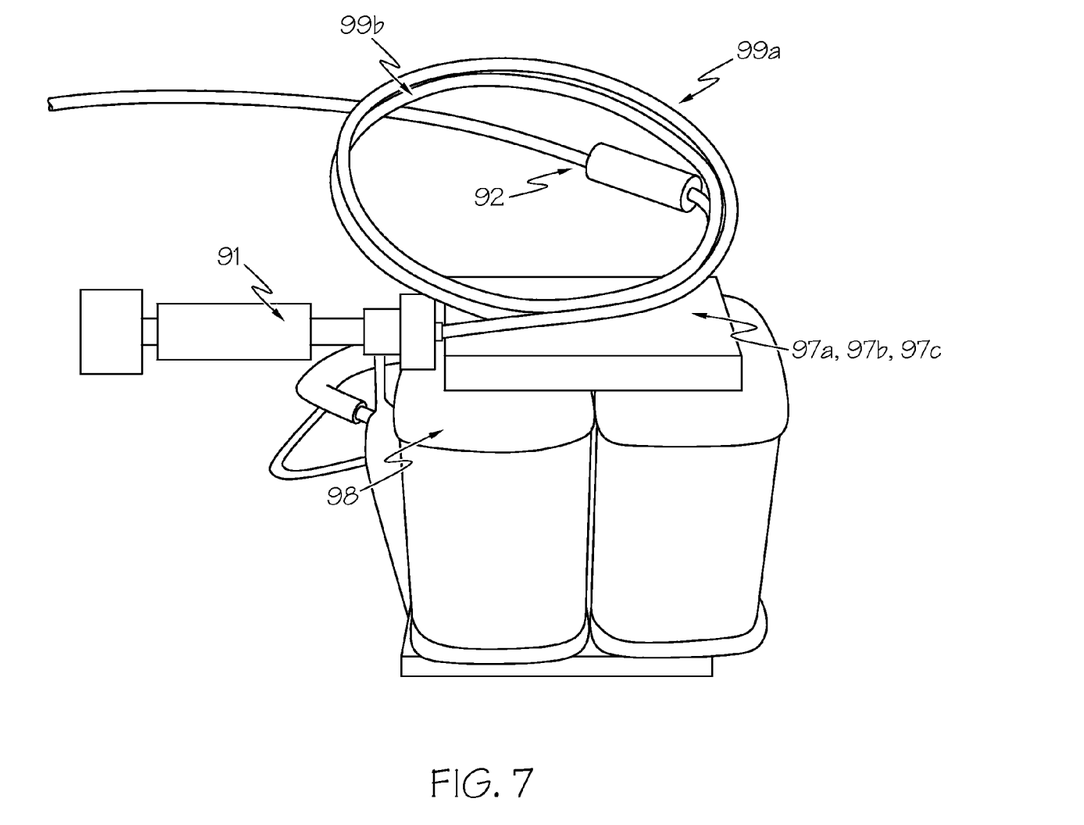

The construction of a particularly preferred device according to the invention is shown in FIG. 2. The device can be constructed to a large extent from commercial HPLC components. One component with a special function is the extractor (90). In a particularly preferred embodiment this is a toroidal core transformer which builds up a strong magnetic field when current flows and on which a HPLC line in the form of a loop is attached (FIG. 7). A HPLC line with an inner diameter between 0.2 mm and 2.0 mm is especially preferred. Preferred materials for the line are polyphenyl sulfone (PPSU), polyether ether ketone (PEEK) and silicone.

Figure 1:
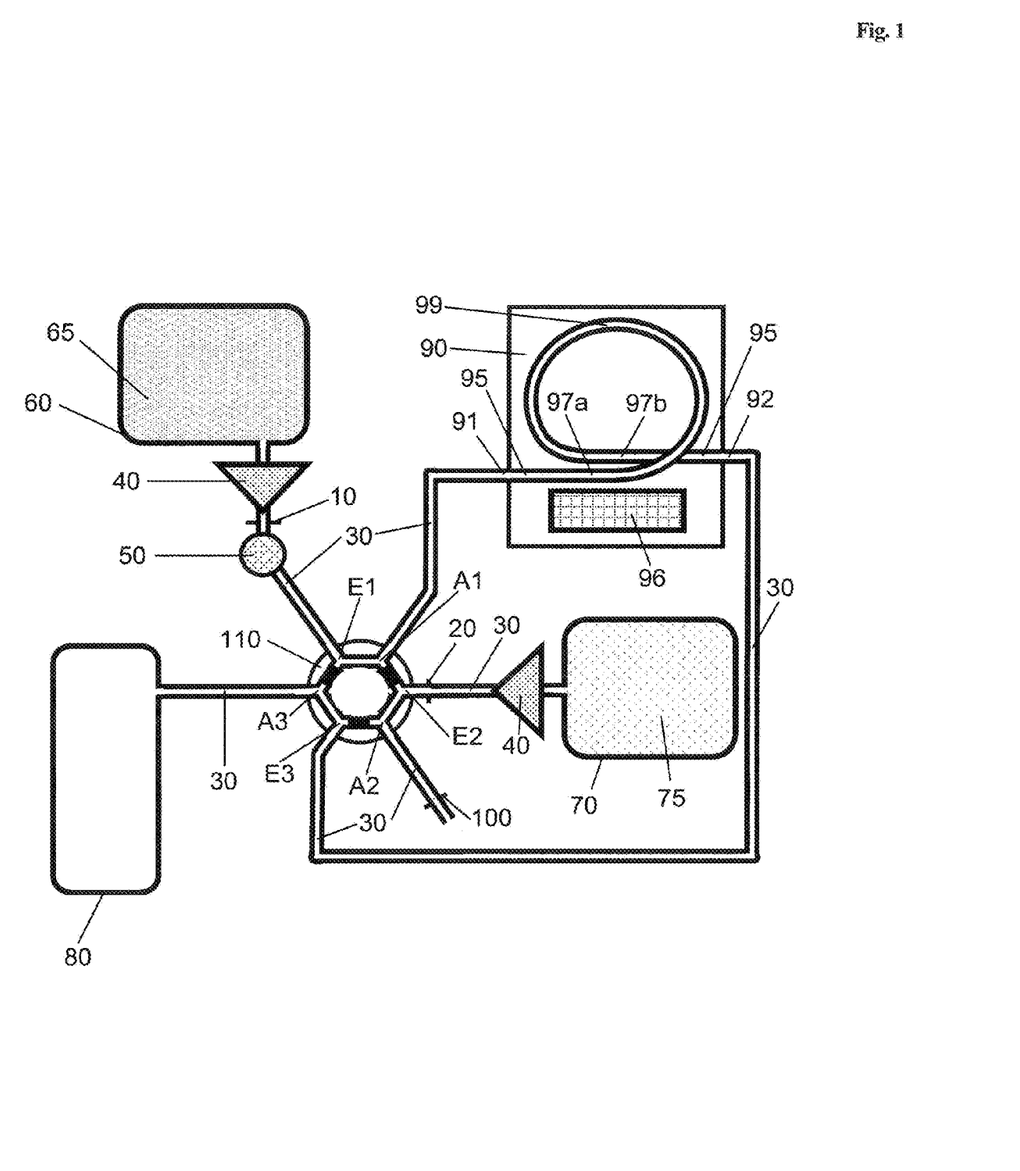
FIG. 1: Device with a liquid system (LS) comprising means for making fluidic connections (30), a first and a second inlet (10, 20), at least one pressure-generating means (40), an injection device (50), two storage containers (60, 70) for a first and a second mobile phase (65, 75) in a liquid state of aggregation, a collecting vessel (80), an extractor (90), an outlet (100) and a means suitable for producing two different fluid connecting states (switching unit, 110). In the preferred embodiment shown the pressure-generating means consists of two pumps which are each arranged between the storage container and inlet. Alternatively it would be possible to pressurize the storage container. In the extractor (90) the line (95) between the entry port (91) and exit port (92) of the extractor (90) has a helical configuration with one winding (99) where each of the sections (97a, 97b) of the line leading to the entry port and exit port are arranged side by side. The sections of the line labelled (97a) and (97b) leading to the entry port (91) and exit port (92) of the extractor are also referred to as a whole as (97).

In other aspects, the invention comprises the following further items as very much preferred embodiments:

1. Device with a liquid system (LS) according to FIG. 1, comprising means for making fluidic connections (30), a first and a second inlet (10, 20), at least one pressure-generating means (40), an injection device (50), two storage containers (60, 70) for a first and a second mobile phase (65, 75) in a liquid state of aggregation, a collecting vessel (80), an extractor (90), an outlet (100) and a means suitable for producing two different fluid connecting states (switching unit, 110), characterized in that the first inlet (10) is designed such that the first mobile phase (65) can be fed under pressure from the first storage container (60) to the LS via a fluidic connection;

the first inlet (10) is additionally fluidically connected to an injection device (50), the injection device being designed such that it allows a mixture (120) of liquid sample material (121) and microparticles suspended therein (122) to be introduced into the first mobile phase that was introduced through the inlet;

the second inlet (20) is designed such that the second mobile phase (75) can be fed under pressure from the second storage container (70) to the LS via a fluidic connection;

the first inlet (10) is connected to a first entry port (E1) of the switching unit (110) and the second inlet (20) is fluidically connected to a second entry port (E2) of the switching unit;

the extractor (90) has one entry port (91) and one exit port (92) where the entry port (91) of the extractor is fluidically connected to a first exit port (A1) of the switching unit and the exit port (92) of the extractor is fluidically connected to a third entry port (E3) of the switching unit;

the extractor additionally comprises a fluid connecting line (95) between the entry port (91) and the exit port (92), also a controllable device (96) which can be used to temporarily apply a local magnetic field to two or more consecutive sections (97a, 97b) of this line;

the second exit port (A2) of the switching unit (110) is the outlet (100) or is fluidically connected to the outlet (100);

the third exit port (A3) of the switching unit (110) is fluidically connected to the collecting vessel (80); and the switching unit (110) is suitable in a first connecting state (I) for fluidically connecting E1 and A1, E2 and A2 as well as E3 and A3 (also referred to as position (1)) and in the second connecting state (II) it is suitable for fluidically connecting E2 and A1, E3 and A2 as well as E1 and A3 (also referred to as position (II)).

2. Device according to item 1 and FIG. 2, characterized in that the LS is a high pressure LS (HLS), the HLS is preferably a substantially closed system and the outlet (100) is fluidically connected to a separation unit (130) and the separation unit is fluidically connected to a detector (140) and the exit port (145) of the detector is fluidically connected to the collecting vessel (80).

3. Device according to item 2, characterized in that the separation unit (130) is a chromatography column.

4. Device according to one of the items 2 or 3, characterized in that the detector (140) is selected from the group comprising UV/Vis spectrometer, diode array detector, light scatter detector, fluorescence detector, refractive index detector, mass spectrometer, conductivity detector, electrochemical detector.

5. Device according to one of the items 1 to 4, characterized in that the controllable device (96) of the extractor (90) comprises an electromagnet.

6. Device according to item 5, characterized in that the line (95) between the entry port (91) and exit port (92) of the extractor (90) is designed as a helix with one winding (99) also referred to as a loop, where each of the sections (97a, 97b) of the line leading to the entry port and exit port are arranged side by side.

7. Device according to item 6 and FIG. 2B, characterized in that the line (95) between the entry port (91) and exit port (92) of the extractor (90) has a helical design and has two or more windings or loops (99a, 99b) where one or more sections (97c) of the windings and each of the sections (97a, 97b) of the line leading to the entry port (91) and exit port (92) are arranged side by side.

8. Device according to one of the items 5 to 7, characterized in that the electromagnet is arranged such that the magnetic field can act on two or more sections (97) of the line (95) arranged side by side between the entry port (91) and exit port (92) of the extractor (90).

9. Device according to one of the items 5 to 8, additionally comprising a control unit and characterized in that the control unit controls the pressure-generating means (40), the switching unit (110) and the electromagnet.

10. Device according to one of the items 2 to 9, characterized in that the pressure-generating means comprises two HPLC pumps.

11. Device according to one of the items 1 to 10, characterized in that the collecting vessel (80) comprises a magnet or electromagnet.

12. Device according to one of the items 1 to 11, additionally comprising a first (65) and a second (75) mobile phase in a liquid state of aggregation.

13. Device according to one of the items 1 to 12, additionally comprising magnetic or paramagnetic microparticles (122).

14. Device according to item 13, characterized in that the microparticles have a functionalized surface (123).

15. Device according to item 14, characterized in that the surface allows the adsorption of an analyte.

16. Device according to item 15, characterized in that the surface of the microparticles is hydrophobic.

17. Device according to item 15, characterized in that the surface of the microparticles is hydrophilic.

18. Device according to item 15, characterized in that the surface is selected from the group comprising anion exchange material, cation exchange material, mixed hydrophobic and hydrophilic copolymers and silica.

19. Device according to item 17, characterized in that the surface comprises C1-C50, preferably C5-C20 hydrocarbon residues.

20. Device according to one of the items 13 to 19 additionally comprising a liquid sample material.

21. Device according to item 20, characterized in that the sample material is a suspension.

22. Device according to item 21, characterized in that the sample material is a homogenate.

23. Device according to one of the items 20 to 22, characterized in that the sample material contains food components, components of a soil sample or waste water.

24. Device according to item 20, characterized in that the sample material comprises a biological liquid, a suspension or a homogenate containing biological material or a lysate of biological material.

25. Device according to item 24, characterized in that the sample material is selected from the group comprising whole blood, citrate blood, heparin blood, EDTA blood, plasma, serum, urine, sputum, synovial liquid, bronchial lavage, respiratory air condensate and liquor.

26. Use of a device according to one of the items 1 to 25 for manipulating magnetic microparticles and two different mobile phases in a liquid state of aggregation.

27. Use according to item 26 additionally for manipulating liquid sample material.

28. Method for obtaining a purified analyte from a complex liquid sample material containing the said analyte comprising the steps
   (a) contacting the liquid sample material (121) containing the analyte with microparticles (122) made of a magnetic or paramagnetic material with a functionalized surface (123) whereby the analyte adsorbs to the surface; followed by
   (b) introducing the sample material with the microparticles into a device according to one of the points 1 to 25 using the injection device (50); followed by
   (c) pumping a first mobile phase (65) from a first storage vessel (60) into the first inlet (10) of the device where the switching unit (110) of the device makes the connecting state (I) and in the extractor (90) a magnetic field is applied to a first section (97a) of the line (95) located therein which is suitable for immobilizing the magnetic or paramagnetic microparticles (122) contained in the mobile phase entering through the line (95) on the nearest inner wall (93) of the line (95) facing the magnetic field in the first section (97a); followed by
   (d) immobilizing the microparticles (122) in the extractor (90) on the inner wall (93) in the first section (97a) of the line; followed by
   (e) separating the microparticles (122) from the remaining sample material by further pumping the first mobile phase (65) from the first storage vessel (60) into the first inlet (10) whereby the immobilized microparticles are washed with the first mobile phase and the remaining sample material is fed into the collecting container (80); followed by
   (f) switching over the switching unit (110) into the connecting state (II) and pumping a second mobile phase (75) from the second storage vessel (70) into the second inlet (20) of the device where the second mobile phase (75) is suitable for detaching the adsorbed analyte from the surface of the microparticles (122); followed by
   (g) eluting the analyte by contacting the microparticles (122) with the second mobile phase (75) and at the same time weakening or removing the magnetic field from the first section (97a) of the line (95) in the extractor (90) and moving the microparticles (122) in the line (95) towards a second section (97b) of the line (95) by the movement of the mobile phase (75);
   (h) applying a magnetic field to the second section (97b) of the line (95) where the magnetic field is suitable for immobilizing magnetic or paramagnetic microparticles (122) contained in the mobile phase entering through the line (95) on the nearest inner wall (93) of the line (95) facing the magnetic field in the second section (97b); followed by (i) immobilizing the microparticles (122) on the inner wall (93) in the second section (97b) of the line; followed by (j) moving the second mobile phase containing the eluted analyte to the outlet (100) of the device by further pumping the second mobile phase (75) from the second storage vessel (70) into the second entry port (20) by means of which the analyte is obtained in a purified form at the outlet (100).

29. Method according to item 28, characterized in that in the device the line (95) between the entry port (91) and the exit port (92) of the extractor (90) has a helical configuration with n (n=2 or more than 2) windings (99), wherein n sections (97c) of the windings and the respective sections (97a, 97b) of the line leading to the entry port (91) and exit port (92) are arranged side by side, the magnetic field can act on the sections of line arranged side by side between the entry port and exit port of the extractor (97a, 97b, 97c) and step (e) is followed by the steps (e') washing the microparticles (122) by further pumping the first mobile phase (65) into the first inlet (10) and simultaneously weakening or removing the magnetic field on the section of the line in the extractor on which the microparticles are immobilized, and moving the microparticles in the line by the movement of the mobile phase towards the next section suitable for an immobilization followed by (e") renewed immobilization of the microparticles by applying a magnetic field to the next section of the line that is suitable for an immobilization;

where (e') and (e") can be carried out n−1 times.

30. Method according to one of the items 28 and 29, characterized in that the first mobile phase is water or an aqueous solution.

31. Method according to one of the items 28 to 30, characterized in that the second mobile phase is an organic solvent.

32. Method according to one of the items 28 to 31, characterized in that the second mobile phase is a nonpolar organic solvent.

33. Method according to one of the items 28 to 31, characterized in that the second mobile phase is a polar organic solvent.

34. Method according to one of the items 28 to 31, characterized in that the second mobile phase is an organic solvent which is selected from the group comprising a C1-C6 aliphatic alcohol, acetonitrile, methyl-tert-butyl ether (MTBE), acetone, ethyl acetate, hexane, dimethyl sulfoxide, diisopropyl ether, dichloromethane, trichloromethane and tetrachloromethane.

35. Method according to one of the items 28 to 34, characterized in that the sample material is a biological fluid, a suspension or a homogenate containing biological material or a lysate of biological material.

36. Method according to item 35, characterized in the sample material is selected from the group comprising whole blood, citrate blood, heparin blood, EDTA blood, plasma, serum, urine, sputum, synovial fluid, bronchial lavage, respiratory air condensate and liquor.

37. Method for detecting an analyte in a complex liquid sample material containing said analyte, comprising the steps (a) providing a device according to one of the items 2 to 25;

(b) obtaining the purified analyte from the sample material using a method according to one of the items 28 to 36, wherein the analyte is obtained in a purified form at the outlet (100) of the device and the switching unit (110) makes the connecting state (II);

(c) moving the second mobile phase containing (i) the analyte and (ii) optionally further substances that were eluted from the microparticles together with the analyte through the separation unit (130) and into the detector (140) where the movement is driven by pumping the second mobile phase (75) from the second storage vessel (70) into the second entry port (20);

(d) detecting the analyte by the detector (140).

38. Method according to item 37, characterized in that step (d) is followed by the steps (e) switching over the switching unit (110) into the connecting state (II);

(f) weakening or removing the magnetic field in the extractor (90);

(g) pumping the first mobile phase (65) from the second storage vessel (60) into the first inlet (10) during which the microparticles (122) are moved towards the collecting vessel (80);

(h) moving the microparticles with the first mobile phase into the collecting vessel.

39. Method according to item 38, characterized in that a device according to one of the items 11 to 18 is used and the microparticles are immobilized in the collecting vessel by a magnetic field.

The following examples, publications and figures further elucidate the invention the protective scope of which is derived from the patent claims. The described devices and processes are to be understood as examples which still describe the subject matter of the invention even after modifications.

EXAMPLE 1

Description of the Use of the Device According to the Invention

In general the device can be designed to be used cyclically where the stages of a cycle can be subdivided as an example into A-D. In this connection reference is made to FIGS. 1-7 and in particular to FIG. 6 A-D.

A—After the mixture of sample material and extraction particles has been injected, the mixture reaches the extractor where the particles (122) are immobilized for the first time. This stage corresponds to the situation in the extractor shown in FIG. 5A. The switching unit is in position (1) as a result of which the first mobile phase is passed into the system. A magnetic field symbolized by the horizontal texture of (96) is applied by means of the device (96).

B—The switching unit is in position (II) as a result of which the second mobile phase is passed into the system. After separation of the remaining sample material from the particles and the change from the first to the second mobile phase, the extraction particles (122) reach the loop of the extractor corresponding to the situation shown in FIG. 5B. In this process step no magnetic field is applied or the magnetic field is reduced to such an extent that the extraction particles are again mobile symbolized by the perpendicular texture of (96). The holding time of the extraction particles in the loop (99) is preferably adjusted such that at least 20%, more preferably at least 30%, even more preferably at least 50% and even more preferably 75% and even more preferably at least 90% of the analyte is eluted into the second mobile phase. For quantitative determinations it is advantageous that the amount of the eluted analyte is proportional to the concentration of the analyte in the sample material for the same elution times.

C—In the subsequent step a magnetic field is again applied to the line in front of the exit port of the extractor (see texture of (96)). The particles (122) suspended in the mobile phase that flows past are again immobilized corresponding to the situation shown in FIG. 5C. The switching unit is also in position (II) in this process step as a result of which the substances (also including the analyte) detached from the particles together with the second mobile phase are conveyed to the separation unit and to the detector. The magnetic field generated by (96) is maintained during this and the particles (122) are retained.

D—After the separation and detection step is completed, the device is regenerated. The switching unit is brought into position (I) and the first mobile phase is passed into (pumped into) the liquid system. In this process step no magnetic field is applied or the magnetic field is reduced to such an extent that the extraction particles are again mobile, symbolized by the perpendicular texture of (96). The particles (122) are transported together with the liquid phase which surrounds them into the collecting vessel (80). The particles can be optionally concentrated in the container by a local magnetic field in order to for example make them more accessible to a recovery.

EXAMPLE 2

Processing and Analysis of Sample Material

Serum as an example of a biological sample material is mixed with a suspension of C18-functionalized ferromagnetic microparticles (extraction particles). In the mixing process analyte molecules of low polarity are adsorbed to the hydrophobic chains of the microparticles. The mixture of sample and particles is injected via an injection valve into the device according to the invention. The first mobile phase of this system is an aqueous solution. The mixture of sample and particles is transferred to an electromagnet by passing in the first mobile phase. Here the ferromagnetic particles loaded with analyte are retained and immobilized in the tubing system with the aid of the activated electromagnet. The non-particle-bound sample matrix is transported by the continuous flow of the first mobile phase into the collecting vessel (waste). The aqueous mobile phase is then replaced in the tubing system by an organic solvent as the second mobile phase with the aid of a 6 port HPLC switching valve. The electromagnet is de-energized for a short period; the particles are resuspended in the organic solvent in the loop of the extractor and the target analyte is detached from the functionalized particles. After a few seconds the electromagnet is again switched on and the particles which have in the meantime become mobile in the tube loop are again immobilized. The target analyte molecules eluted from the particles are transferred directly onto an analytic chromatography column. A chromatographic detector is connected in series to this separation column. A prototype of an extraction system was constructed on the basis of this working principle and its extractor is shown in FIG. 7.

EXAMPLE 3

Test Measurement Using the Device According to the Invention

The antimicrobial pharmacological agent itraconazole was examined as an example of an analyte of in-vitro diagnostics. This substance was quantified in a therapeutic concentration range from a human sample matrix. For this purpose serum samples containing known itraconazole concentrations determined by means of LC tandem mass spectrometry as well as "drug-free" sera were examined.

C18-modified magnetic or paramagnetic extraction particles from the Dynal Company (Oslo, Norway) were used (Dynabeads® 18, 50 mg/ml). 15 µl of this bead suspension was pipetted into a reaction vessel; this was positioned on a permanent magnetic particle extractor (Dynal MPC-S Magnetic Particle Concentrator). The particle-free solvent medium was removed. The particles were then washed twice with 200 µl 0.1% trichloroacetic acid in each case; for this purpose the reaction vessel was repeatedly removed from the extractor and again positioned therein in order to immobilize the particles. Finally the particles were suspended in 1000 µl water.

In order to analyse the serum samples using the system described in the present invention, 15 µl sample was mixed with 15 µl of the prepared aqueous particle suspension in a reaction vessel. This mixture was in each case injected into the described device by a manual injection valve and processed according to the work process described above. The aspiration of sample aliquots, the mixing of sample and extraction particles and the injection which are carried out manually in a first prototype setup can also be carried out fully automatically using a conventional autosampler.

Figure 8A:
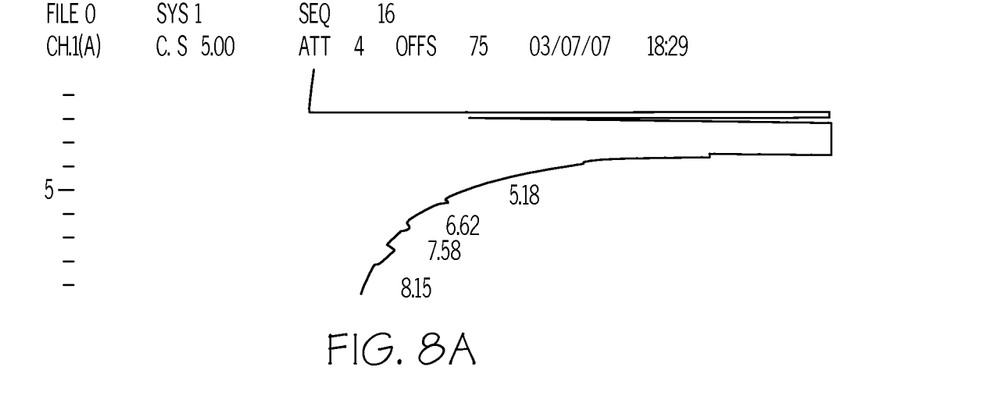
FIG. 8: Examples of chromatograms of samples which were processed and analysed with the aid of a high-pressure liquid system according to the invention with an attached separation and detection unit (see example 3). The X axis shows the retention time and the Y axis shows the absorption measured on the UV spectrometer. A—Chromatogram of a "drug-free" patient sample; B—Chromatogram of the calibrator sample with a set itraconazole concentration of 2.9 mg/l. The peak area comprises 81234 counts and the retention time is 6.56 min.; C—Chromatogram of the analysed patient sample. The determined itraconazole concentration is 2.0 mg/l. The peak area comprises 56352 counts and the retention time is 6.56 min.
Figure 8B:
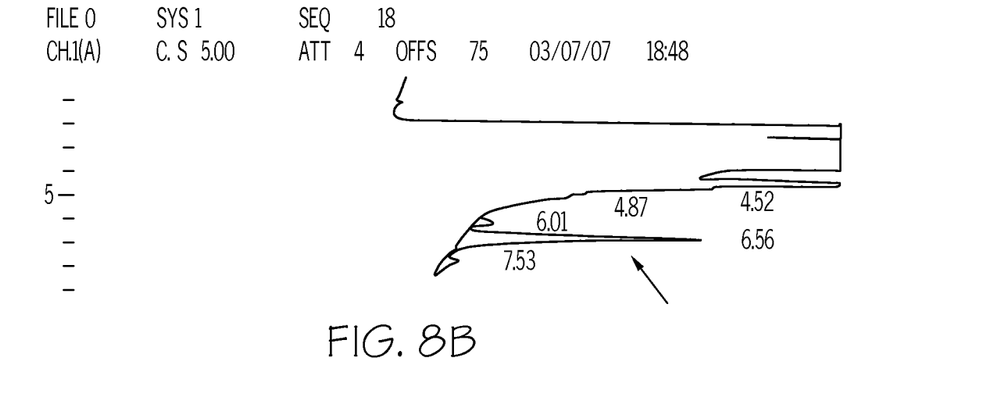
Figure 8C:
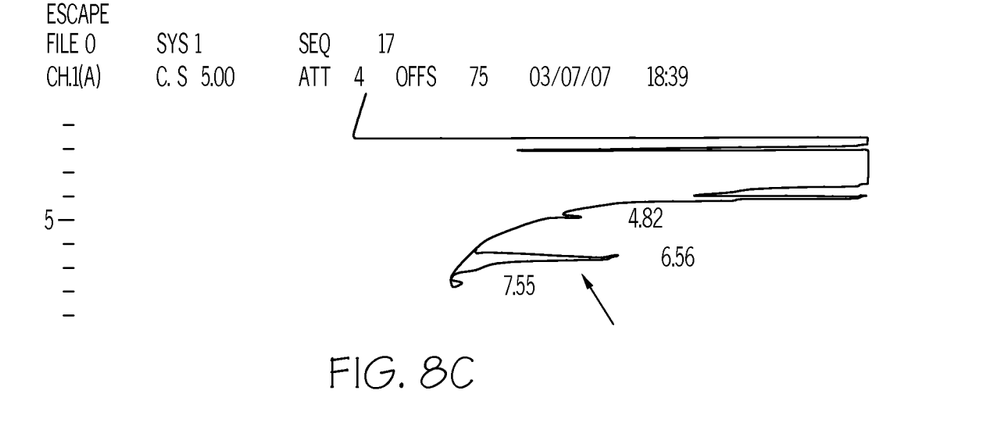

FIGS. 8 A-C show examples of chromatograms of the analysis of a blank sample (a), a calibrator sample (b) containing an itraconazole concentration of 2.9 mg/l as well as a pooled patient sample (c). When the patient sample is quantified on the basis of the calibrator sample, a concentration of 2.0 mg/l is calculated. The same result was found for this sample using a recognized mass spectrometric analytical method for determining itraconazole (Vogeser M, Spöhrer U, Schiel X. Determination of itraconazole and hydroxyitraconazole in plasma by use of liquid chromatography-tandem mass spectrometry with on-line solid-phase extraction. Clin. Chem. Lab. Med. 2003; 41:915-20).

What is claimed is:
1. A liquid system (LS) comprising:
a first and a second inlet,
a rotary valve switching unit suitable for producing two different fluid connecting states,
an extractor with an entry port and an exit port, and with a controllable device which can be used to temporarily apply a local magnetic field,
wherein the extractor comprises a fluid connecting line between the entry port and the exit port, and the controllable device is capable of temporarily applying a local magnetic field to two or more consecutive sections of the line,
at least one pressure-generating means, an injection device, two storage containers for a first and a second mobile phase in a liquid state of aggregation, a collecting vessel, and an outlet, wherein
the first inlet is designed such that the first mobile phase can be fed under pressure from the first storage container to the rotary valve switching unit via a fluidic connection;
the first inlet is additionally fluidically connected to an injection device, the injection device being designed such that it allows a mixture of liquid sample material and microparticles suspended therein to be introduced into the first mobile phase that was introduced through the first inlet;

the second inlet is designed such that the second mobile phase can be fed under pressure from the second storage container to the rotary valve switching unit via a another fluidic connection;

the first inlet is fluidically connected to a first entry port of the rotary valve switching unit and the second inlet is fluidically connected to a second entry port of the rotary valve switching unit;

the entry port of the extractor is fluidically connected to a first exit port of the rotary valve switching unit and the exit port of the extractor is fluidically connected to a third entry port of the rotary valve switching unit;

a second exit port of the rotary valve switching unit is the outlet or is fluidically connected to the outlet;

a third exit port of the rotary valve switching unit is fluidically connected to the collecting vessel; and the rotary valve switching unit is suitable in a first connecting state (I) for fluidically connecting the first entry port and the first exit port, the second entry port and the second exit port as well as the third entry port and the third exit port and in the second connecting state (II) it is suitable for fluidically connecting the second entry port and the first exit port, the third entry port and the second exit port as well as the first entry port and the third exit port.

2. The device according to claim 1, wherein the LS is a high pressure LS (HLS), the HLS is a substantially closed system and the outlet is fluidically connected to a separation unit and the separation unit is fluidically connected to a detector and the exit port of the detector is fluidically connected to the collecting vessel.

3. The device according to claim 2, wherein the separation unit is a chromatography column.

4. The device according to claim 2, wherein the detector is selected from the group comprising UV/Vis spectrometer, diode array detector, light scatter detector, fluorescence detector, refractive index detector, mass spectrometer, conductivity detector, electrochemical detector.

5. The device according to claim 1, wherein the controllable device of the extractor comprises an electromagnet.

6. The device according to claim 5, wherein the electromagnet is arranged such that the magnetic field can act on two or more sections of the line arranged side by side between the entry port and exit port of the extractor.

7. The device according to claim 1, additionally comprising a first and a second mobile phase in a liquid state of aggregation.

8. The device according to claim 1, additionally comprising magnetic or paramagnetic microparticles.

9. The device according to claim 8, additionally comprising a liquid sample material.

10. A method for obtaining a purified analyte from a complex liquid sample material containing the analyte comprising the steps of
a. contacting the liquid sample material containing the analyte with microparticles made of a magnetic or paramagnetic material with a functionalized surface whereby the analyte adsorbs to the surface;
b. introducing the sample material with the microparticles into the device according to claim 1 via the injection device;
c. pumping a first mobile phase from the first storage container into the first inlet of the device where the switching unit of the device makes the connecting state (I) and in the extractor a magnetic field is applied to a first section of the line located therein which is suitable for immobilizing the magnetic or paramagnetic microparticles contained in the first mobile phase entering through the line on the nearest inner wall of the line facing the magnetic field in the first section;
d. immobilizing the microparticles in the extractor on the inner wall in the first section of line;
e. separating the microparticles from the remaining sample material by further pumping the first mobile phase from the first storage container into the first inlet whereby the immobilized microparticles are washed with the first mobile phase and the remaining sample material is fed into the collecting container;
f. switching over the switching unit into the connecting state (II) and pumping a second mobile phase from the second storage container into the second inlet of the device where the second mobile phase is suitable for detaching the adsorbed analyte from the surface of the microparticles;
g. eluting the analyte by contacting the microparticles with the second mobile phase and at the same time weakening or removing the magnetic field from the first section of the line in the extractor and moving the microparticles in the line towards a second section of the line by the movement of the second mobile phase;
h. applying a magnetic field to the second section of the line where the magnetic field is suitable for immobilizing magnetic or paramagnetic microparticles contained in the mobile phase entering through the line on the nearest inner wall of the line facing the magnetic field in the second section;
i. immobilizing the microparticles on the inner wall in the second section of the line; and
j. moving the second mobile phase containing the eluted analyte to the outlet of the device by further pumping the second mobile phase from the second storage vessel into the second entry port by means of which the analyte is obtained in a purified form at the outlet.

11. The method according to claim 10, wherein step (e) is followed by the steps
(e') washing the microparticles by further pumping the first mobile phase into the first inlet and simultaneously weakening or removing the magnetic field on the section of the line in the extractor on which the microparticles are immobilized, and moving the microparticles in the line by the movement of the mobile phase towards the next section suitable for an immobilization, and
(e") renewed immobilization of the microparticles by applying a magnetic field to the next section of the line that is suitable for an immobilization;
where (e') and (e") can be carried out n−1 times,
whereby in the device the line between the entry port and the exit port of the extractor has a helical configuration with n (n=2 or more than 2) windings, wherein n sections of the windings and the respective sections of the line leading to the entry port and exit port are arranged side by side, the magnetic field can act on the sections of line arranged side by side between the entry port and exit port of the extractor.

12. The method according to claim 10, wherein the sample material comprises a biological liquid, a suspension containing a biological material or a lysate of biological material.

13. A method for obtaining a purified analyte from a complex liquid sample material containing the analyte comprising the steps of
a. contacting the liquid sample material containing the analyte with microparticles made of a magnetic or paramagnetic material with a functionalized surface whereby the analyte adsorbs to the surface;

b. introducing the sample material with the microparticles into the device according to claim 2 via the injection device;
c. pumping a first mobile phase from the first storage container into the first inlet of the device where the switching unit of the device makes the connecting state (I) and in the extractor a magnetic field is applied to a first section of the line located therein which is suitable for immobilizing the magnetic or paramagnetic microparticles contained in the first mobile phase entering through the line on the nearest inner wall of the line facing the magnetic field in the first section;
d. immobilizing the microparticles in the extractor on the inner wall in the first section of line;
e. separating the microparticles from the remaining sample material by further pumping the first mobile phase from the first storage container into the first inlet whereby the immobilized microparticles are washed with the first mobile phase and the remaining sample material is fed into the collecting container;
f. switching over the switching unit into the connecting state (II) and pumping a second mobile phase from the second storage container into the second inlet of the device where the second mobile phase is suitable for detaching the adsorbed analyte from the surface of the microparticles;
g. eluting the analyte by contacting the microparticles with the second mobile phase and at the same time weakening or removing the magnetic field from the first section of the line in the extractor and moving the microparticles in the line towards a second section of the line by the movement of the second mobile phase;
h. applying a magnetic field to the second section of the line where the magnetic field is suitable for immobilizing magnetic or paramagnetic microparticles contained in the mobile phase entering through the line on the nearest inner wall of the line facing the magnetic field in the second section;
i. immobilizing the microparticles on the inner wall in the second section of the line;
j. moving the second mobile phase containing the eluted analyte to the outlet of the device by further pumping the second mobile phase from the second storage vessel into the second entry port by means of which the analyte is obtained in a purified form at the outlet; and
k. moving the second mobile phase containing the analyte through the separation unit and into the detector where the movement is driven by pumping the second mobile phase from the second storage vessel into the second entry port, and detecting the analyte by the detector.

* * * * *